(12) United States Patent
Skafidas et al.

(10) Patent No.: US 11,703,436 B2
(45) Date of Patent: Jul. 18, 2023

(54) BIOLOGICAL FLUID SAMPLE ASSESSMENT

(71) Applicant: MX3 Diagnostics, Inc., Austin, TX (US)

(72) Inventors: Efstratios Skafidas, Melbourne (AU); Hsien Ming, Melbourne (AU); You Liang, Melbourne (AU); Duc Huynh, Melbourne (AU); Thanh Nguyen, Melbourne (AU); Michael Erlichster, Melbourne (AU)

(73) Assignee: MX3 Diagnostics, Inc., Austin, TX (US)

( * ) Notice: Subject to any disclaimer, the term of this patent is extended or adjusted under 35 U.S.C. 154(b) by 32 days.

(21) Appl. No.: 17/159,770

(22) Filed: Jan. 27, 2021

(65) Prior Publication Data

US 2021/0239586 A1 Aug. 5, 2021

Related U.S. Application Data

(60) Provisional application No. 62/967,694, filed on Jan. 30, 2020.

(51) Int. Cl.
*G01N 11/02* (2006.01)
*G01N 33/493* (2006.01)
(Continued)

(52) U.S. Cl.
CPC ....... *G01N 11/02* (2013.01); *G01N 33/48707* (2013.01); *G01N 33/49* (2013.01); *G01N 33/493* (2013.01)

(58) Field of Classification Search
CPC .................. G01N 11/02; G01N 33/493; G01N 33/48707; G01N 33/49; G01N 11/04; G01N 33/487
(Continued)

(56) References Cited

U.S. PATENT DOCUMENTS 4,454,007 A 6/1984 Pace
5,714,341 A 2/1998 Thieme et al.
(Continued)

FOREIGN PATENT DOCUMENTS

CN 109682878 A 4/2019
EP 1710565 A1 10/2006
(Continued)

OTHER PUBLICATIONS

"Cepheid and Sherlock Biosciences Establish Collaboration on New GeneXpert Tests for Infectious Diseases and Oncology Leveraging CRISPR Technology, http://cepheid.mediaroom.com/2020-02-28-Cepheid-and-Sherlock-Biosciences-Establish-Collaboration-on-New-GeneXpert-Tests-for-Infectious-Diseases-and-Oncology-Leveraging-CRISPR-Technology, 3 pages (Feb. 28, 2020)."
(Continued)

*Primary Examiner* — Robert R Raevis
(74) *Attorney, Agent, or Firm* — Knobbe, Martens, Olson & Bear LLP

(57) ABSTRACT

A method of assessing a bodily fluid sample on a test strip may involve applying a periodic signal with a first electrode located at a first location in a microfluidic channel of the test strip, monitoring the applied periodic signal with a second electrode located at a second location in the microfluidic channel, and using a third electrode located at a third location in the microfluidic channel as a reference electrode. The method may also include: collecting the bodily fluid sample in the microfluidic channel; continuing to apply the periodic signal, monitor the periodic signal and use the third electrode as a reference electrode while collecting the bodily fluid sample; and determining that the bodily fluid sample is sufficient for analyzing, based at least in part on the applied and monitored periodic signal.

14 Claims, 3 Drawing Sheets

(51) Int. Cl.
*G01N 33/487* (2006.01)
*G01N 33/49* (2006.01)

(58) Field of Classification Search
USPC ........... 73/54.02, 54.01, 54.07, 54.08, 64.56, 73/61.61, 61.59, 61.41, 61.43, 863, 73/861.05, 198; 600/300; 324/693, 694, 324/697, 705, 706, 717
See application file for complete search history.

(56) References Cited

U.S. PATENT DOCUMENTS

| | | | |
|---|---|---|---|
| 6,086,748 | A | 7/2000 | Durst et al. |
| 6,102,872 | A | 8/2000 | Doneen et al. |
| 6,554,982 | B1 | 4/2003 | Shin et al. |
| 9,546,973 | B2 | 1/2017 | Mcilrath |
| 10,197,523 | B2 | 2/2019 | Huang et al. |
| 10,258,278 | B2 | 4/2019 | Howell et al. |
| 10,989,724 | B1 | 4/2021 | Holmes et al. |
| 2001/0032785 | A1 | 10/2001 | Cha et al. |
| 2002/0011408 | A1 | 1/2002 | Lee et al. |
| 2002/0060247 | A1* | 5/2002 | Krishnaswamy ...... G16H 40/63 235/472.01 |
| 2002/0065332 | A1 | 5/2002 | Choi et al. |
| 2003/0150745 | A1 | 8/2003 | Teodorczyk et al. |
| 2003/0171697 | A1 | 9/2003 | Smith et al. |
| 2004/0238358 | A1 | 12/2004 | Forrow et al. |
| 2005/0143675 | A1 | 6/2005 | Neel et al. |
| 2005/0279647 | A1 | 12/2005 | Beaty |
| 2006/0137980 | A1 | 6/2006 | Lauks et al. |
| 2007/0015287 | A1 | 1/2007 | Robbins et al. |
| 2007/0048224 | A1 | 3/2007 | Howell et al. |
| 2007/0073127 | A1 | 3/2007 | Kiani et al. |
| 2007/0098600 | A1 | 5/2007 | Kayyem |
| 2007/0272564 | A1* | 11/2007 | Huang ............... G01N 27/3273 205/792 |
| 2008/0118397 | A1 | 5/2008 | Slowey et al. |
| 2009/0024060 | A1 | 1/2009 | Darrigrand et al. |
| 2009/0173629 | A1 | 7/2009 | Kidwell |
| 2010/0176006 | A1 | 7/2010 | Bickford et al. |
| 2010/0249652 | A1* | 9/2010 | Rush .................... A61B 5/151 600/583 |
| 2011/0162978 | A1 | 7/2011 | Cardosi et al. |
| 2012/0067741 | A1* | 3/2012 | Kranendonk ...... G01N 27/4163 204/403.01 |
| 2012/0083711 | A1 | 4/2012 | Goldstein et al. |
| 2012/0109011 | A1 | 5/2012 | Cogan et al. |
| 2012/0165626 | A1 | 6/2012 | Irina et al. |
| 2012/0282616 | A1 | 11/2012 | Zeijlstra et al. |
| 2012/0289863 | A1 | 11/2012 | Goldstein et al. |
| 2013/0199944 | A1 | 8/2013 | Petisee |
| 2013/0233061 | A1 | 9/2013 | Sullivan |
| 2013/0341186 | A1 | 12/2013 | Hsu |
| 2014/0277291 | A1 | 9/2014 | Pugh et al. |
| 2014/0326037 | A1 | 11/2014 | Fukuda et al. |
| 2015/0091592 | A1 | 4/2015 | Elder |
| 2015/0216471 | A1 | 8/2015 | Goldstein et al. |
| 2015/0217115 | A1 | 8/2015 | Avitall |
| 2015/0226695 | A1 | 8/2015 | Bakker et al. |
| 2015/0226752 | A1 | 8/2015 | Nazareth et al. |
| 2015/0359458 | A1 | 12/2015 | Erickson et al. |
| 2016/0011178 | A1 | 1/2016 | Hoenes et al. |
| 2016/0120468 | A1 | 5/2016 | Mathew et al. |
| 2016/0266102 | A1 | 9/2016 | Knopfmacher |
| 2016/0320326 | A1 | 11/2016 | Zevenbergen et al. |
| 2016/0361001 | A1 | 12/2016 | Tai et al. |
| 2017/0014822 | A1 | 1/2017 | Ker |
| 2017/0027506 | A1 | 2/2017 | Howell et al. |
| 2017/0067889 | A1 | 3/2017 | Tamir |
| 2017/0138962 | A1 | 5/2017 | Southern |
| 2017/0261461 | A1 | 9/2017 | Bychkova et al. |
| 2018/0125400 | A1 | 5/2018 | Yang et al. |
| 2018/0220947 | A1 | 8/2018 | Bedell, Jr. |
| 2019/0150836 | A1 | 5/2019 | Skafidas et al. |
| 2020/0011851 | A1 | 1/2020 | Piasio et al. |
| 2020/0116664 | A1 | 4/2020 | Abeyrathne |
| 2020/0383582 | A1 | 12/2020 | Bychkov |
| 2021/0005233 | A1 | 1/2021 | Kim et al. |
| 2021/0005322 | A1 | 1/2021 | Huynh et al. |
| 2021/0007646 | A1 | 1/2021 | Nguyen et al. |
| 2021/0215662 | A1 | 7/2021 | Erlichster et al. |
| 2021/0223239 | A1 | 7/2021 | De et al. |
| 2022/0013212 | A1 | 1/2022 | Tseng et al. |
| 2022/0122743 | A1 | 4/2022 | Erlichster et al. |
| 2022/0143609 | A1 | 5/2022 | Xu et al. |

FOREIGN PATENT DOCUMENTS

| | | |
|---|---|---|
| EP | 2075339 A1 | 7/2009 |
| KR | 20160035584 A | 3/2016 |
| WO | WO2010045247 A1 | 4/2010 |
| WO | WO2011075711 A1 | 6/2011 |
| WO | WO2014176753 A1 | 11/2014 |

OTHER PUBLICATIONS

"Cepheid, Xpert Carba-R, GXCARBAR-10, https://www.cepheid.com/Package%20Insert20Files/Xpert-Carba-R-RX-Only-US-IVD-ENGLISH-Package-Insert-301-2438-Rev-F.pdf, Rev. F, 54 pages (Aug. 2019)."

Erlichster et al., "Pan-Family Assays for Rapid Viral Screening: Reducing Delays in Public Health Responses During Pandemics", Clinical Infectious Diseases, Jul. 20, 2020 (Jul. 20, 2020), pp. 1-6, XP055830068.

Nguyen et al., "Saliva Test Strip and Method" U.S. Appl. No. 62/872,339, filed Jul. 10, 2019, 31 pages.

Paul K et al., "The arrival of a true point-of-care molecular assay-ready for global implementation?", Nov. 1, 2015 (Nov. 1, 2015), pages e663-e664, XP055830065.

Skafidas et al., "Biological Fluid Sample Assessment," U.S. Appl. No. 62/967,694, filed Jan. 30, 2020, 21 pages.

Erlichster et al., "Personalized Hydration Assessment and Fluid Replenishment," U.S. Appl. No. 52/876,263, filed Jul. 19, 2019, 30 pages.

Erlichster et al., "Personalized Hydration Assessment and Fluid Replenishment," U.S. Appl. No. 52/957,527, filed Jan. 6, 2020, 35 pages.

Erlichster et al., "Assessment of Biomarker Concentration in a Fluid," U.S. Appl. No. 62/961,438, filed Jan. 15, 2020, 22 pages.

International Search Report and Written Opinion for PCT Application No. PCT/US2021/015282, dated May 25, 2021, 3 pages.

Oncescu et al., "Smartphone based health accessory for colorimetric detection of biomarkers in sweat and saliva," Lab an a Chip 13(16):3232-3238, Jun. 7, 2013.

A. Moya, et al., "Flexible Microfluidic Bio-Lab-on-a-Chip Multi-Sensor Platform for Electrochemical Measurements", Sensors, 2014 IEEE, pp. 1018-1021 (Year: 2014).

* cited by examiner

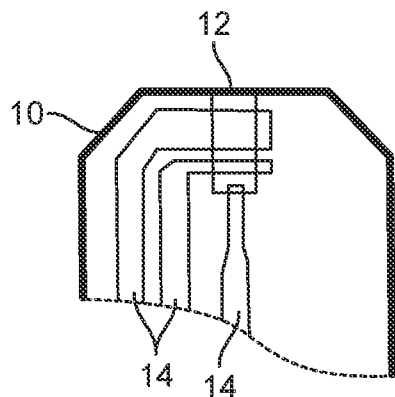 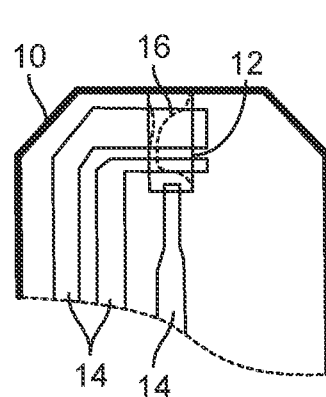 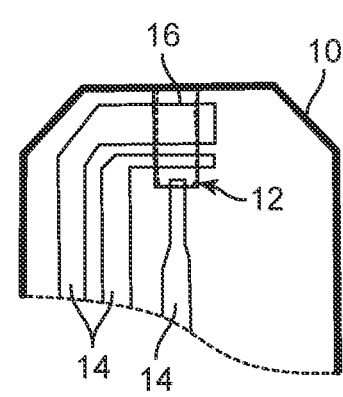
FIG. 1A   FIG. 1B   FIG. 1C
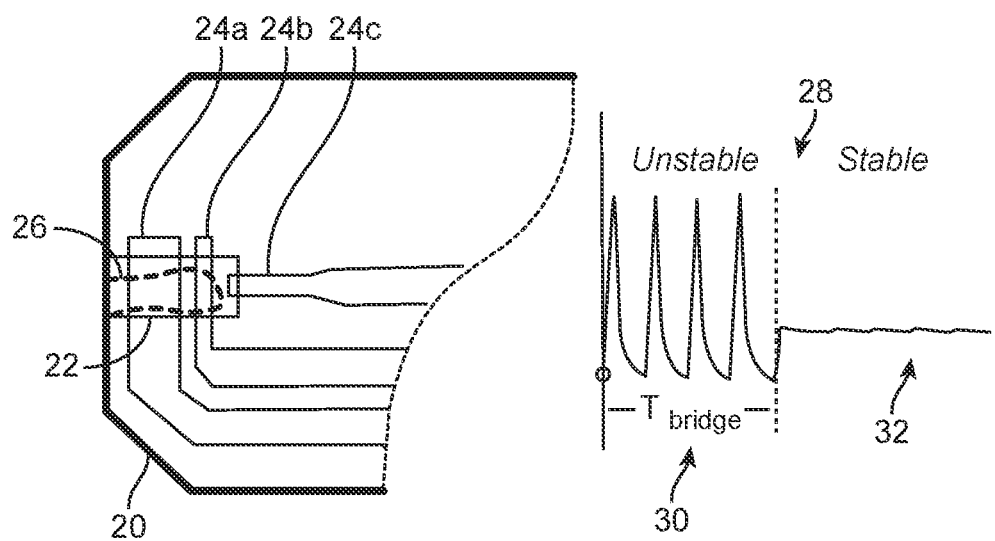
FIG. 2A   FIG. 2B

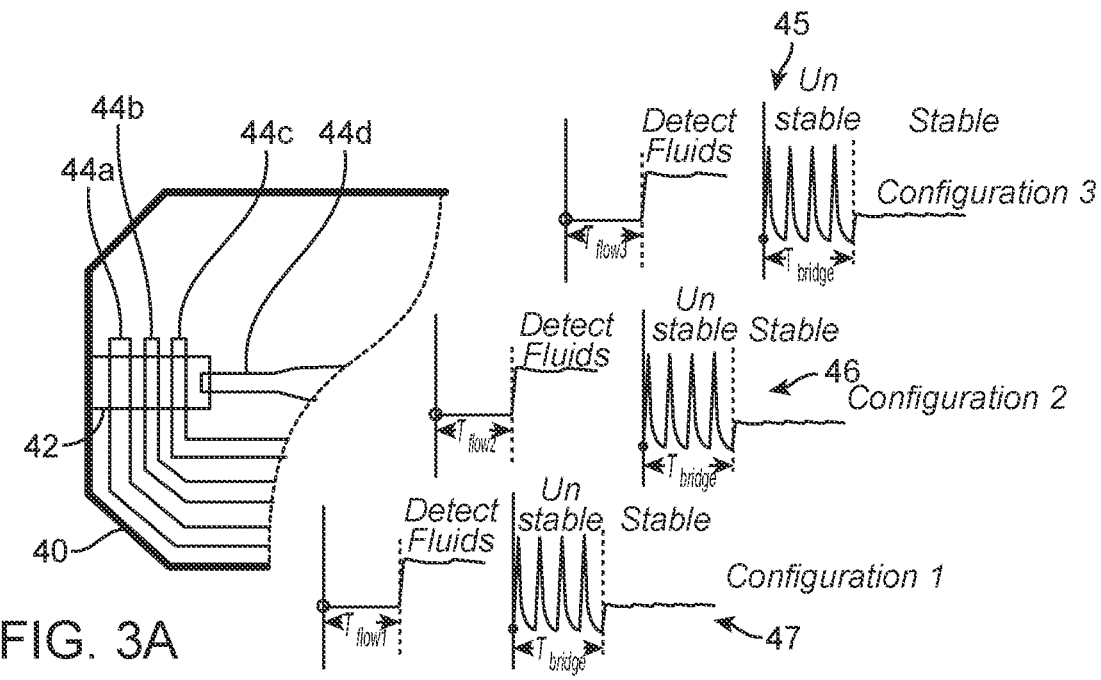
FIG. 3A
FIG. 3B
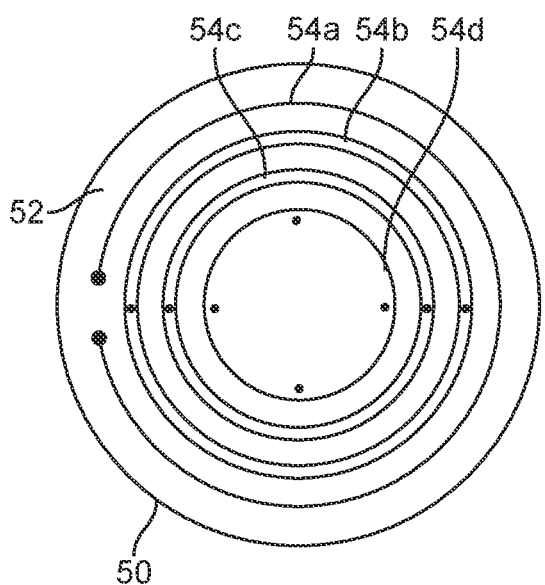
FIG. 4A
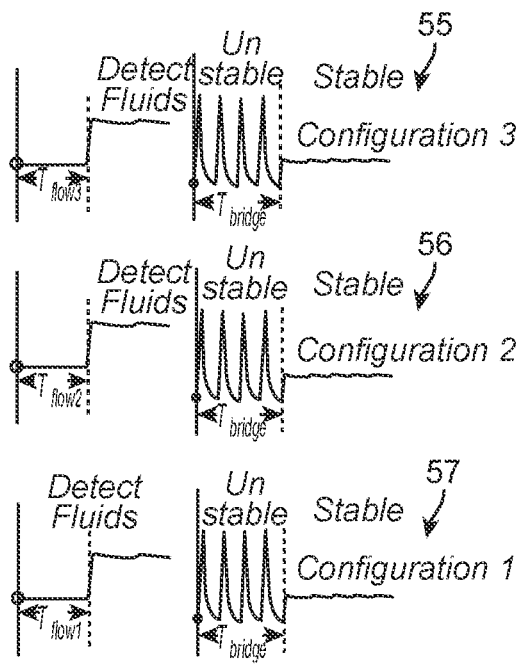
FIG. 4B

BIOLOGICAL FLUID SAMPLE ASSESSMENT

CROSS-REFERENCE TO RELATED APPLICATIONS

This application claims the benefit of U.S. Provisional Patent Application No. 62/967,694, filed Jan. 30, 2020, entitled, "BIOLOGICAL FLUID SAMPLE ASSESSMENT." The disclosure of this priority application is hereby incorporated by reference in its entirety into the present application.

TECHNICAL FIELD

This application describes biomedical systems and methods. More specifically, the application describes a method and system for assessing a bodily fluid sample to determine if it is sufficient for testing.

BACKGROUND

Appropriate hydration in the human body is vital for health and proper functioning of the body organs. Water is lost from the body during respiration, perspiration and urination. Fluid loss of just a few percent can negatively impact cardiovascular function, thermal dissipation, and exercise performance. Dehydration can cause headaches, light-headedness, dizziness, fainting and in extreme cases delirium, unconsciousness or death. Hyponatremia ("over-hydration") can also detrimentally affect the body's functioning, particularly during exercise, and can even lead to death in extreme cases.

Dehydration is an excessive loss of body fluid. In physiological terms, dehydration may entail a deficiency of fluid within an organism. Dehydration can be caused by losing too much fluid, not drinking enough fluids, or both. Vomiting, diarrhea, and excessive perspiration without sufficient liquid intake are other causes of dehydration, which may be particularly worrisome for athletes and people that work under hot, dry conditions. There are three main types of dehydration: hypotonic (primarily a loss of electrolytes, especially sodium), hypertonic (primarily a loss of water), and isotonic (equal loss of water and electrolytes). While isotonic dehydration is the most common, distinction between the three types of dehydration may be important for administering proper treatment.

Relying on thirst as a feedback mechanism to trigger demand for fluid intake may not be adequate to maintain an optimal hydration level, since a sensation of thirst sufficient to cause a subject to drink is often not triggered until after the subject is already dehydrated. This is why marathon runners, for example, are always told to "drink before you feel thirsty." At the same time, drinking too much water during an endurance event like a marathon can lead to hyponatremia, which has led to a number of deaths during such events in the past. Unfortunately, there are currently no practical, affordable, non-invasive devices for measuring a person's hydration level. Measurement devices are typically large and/or expensive devices housed in laboratories, which use blood or urine to measure hydration. This makes measuring hydration impractical, invasive, and/or prohibitively expensive.

Additionally, many other physiological parameters and levels of various substances in the human or animal body are frequently tested or would be desirable to test for. Unfortunately, it is often necessary to sample blood, urine or other bodily substances, such as cerebrospinal fluid, to measure these parameters. Some physiological parameters involve even more invasive or costly measurement techniques.

Therefore, it would be highly beneficial to have a practical, affordable, non-invasive system and method for measuring a person's hydration level. It would also be very desirable to have practical, affordable, non-invasive systems and methods for testing other parameters in the body.

Point-of-care testing systems allow for measurement of biomarkers (e.g., metabolites, hormones, and electrolytes) in biological samples outside of a laboratory, such as a in a clinic or personal residence. By reducing labor and transport costs, point-of-care testing is an attractive alternative to laboratory testing, especially for frequent or routine tests.

Conventional laboratory tests allow for extensive treatment and processing of samples, to normalize sample characteristics and remove any contaminants prior to analysis. With point-of-care tests, on the other hand, extensive sample processing is difficult if not impossible, due to the equipment, cost, and time required. Ideally, therefore, a point-of-care test would use an unprocessed sample, rather than a processed sample.

For some biological fluids, viscosity is strongly regulated by the body. Blood, for example is typically 3-4 centipoise (cP) in viscosity. In contrast, saliva viscosity is less regulated and can range from 1 to 10 cP, depending individual physiology, age, gender, health status, and diet. While this variability can be normalized through laboratory processing (e.g., freezing saliva precipitates mucins, which can then be removed through centrifugation), it presents challenges when designing tools that directly measure analytes in saliva through direct sampling (sampling from the oral cavity) or near-direct sampling (sampling from a recently collected sample).

One specific challenge in analyzing saliva samples using point-of-care systems is the presence of bubbles in the saliva samples. This is particularly the case in individuals with dryer mouths or highly viscous saliva. Bubbles may cause voids in the fluidic channels of a sample analysis device, resulting in blockages or aberrant measurements. Another challenge is the non-uniform flow of more viscous saliva, which may result in incomplete filling of the sampling fluidics.

It would therefore be desirable to develop a device, system and method for assessing whether a bodily fluid sample is adequate for measurement and analysis. Ideally, such devices, systems and methods would be sufficiently easy to use and cost effective to allow them to be used in a point-of-care setting, such as a home, office, gym, or the like, by an untrained user.

SUMMARY

This application describes a device, system and method that use a continuous application of a periodic signal prior to and during sample collection by an electrode. The method also provides for continuous monitoring of the sample collection by a second electrode. Some embodiments also provide for assessment of signal fluctuation during sample collection. Typically, the method requires a period of signal consistency within set bounds prior to initiation of measurement. These features help ensure not only that a sample has completed a circuit between two electrodes prior to measurement initiation, but also that the fluid is no longer being collected and the collected fluid is no longer moving within the sampling fluidics.

In one aspect of the present disclosure, a method of assessing a bodily fluid sample on a test strip involves:

applying a periodic signal with a first electrode located at a first location in a microfluidic channel of the test strip; monitoring the applied periodic signal with a second electrode located at a second location in the microfluidic channel; and using a third electrode located at a third location in the microfluidic channel as a reference electrode, wherein each of the first electrode, the second electrode and the third electrode has a fixed function. The method further involves: collecting the bodily fluid sample in the microfluidic channel; continuing to apply the periodic signal, monitor the periodic signal and use the third electrode as a reference electrode, while collecting the bodily fluid sample; and determining that the bodily fluid sample is sufficient for analyzing, based at least in part on the applying and monitoring of the periodic signal.

In some embodiments, the periodic signal fluctuates depending on a volume of the bodily fluid sample and a movement of the bodily fluid sample through the microfluidic channel, and a period of stability in the monitored periodic signal is required before determining that the bodily fluid sample is sufficient. The method may further involve initiating an analysis of the bodily fluid sample, based on the determining step. Some embodiments may involve, before the determining step: determining that the bodily fluid sample is insufficient for analyzing; and indicating to a user to continue collecting more of the bodily fluid sample on the test strip. For example, determining that the bodily fluid sample is insufficient may involve identifying a period of instability or a period of stability of the monitored periodic signal, outside of an allowed range. Indicating to the user may involve providing an auditory signal, a vibration and/or a visual signal in a bodily fluid analysis device directly connected with the test strip or a separate device wireless connected with the bodily fluid analysis device. In various embodiments, the bodily fluid sample may be any suitable bodily fluid, such as but not limited to saliva, sweat, blood or urine.

In another aspect of the present disclosure, a method of assessing a bodily fluid sample on a test strip involves: applying a periodic signal with a first electrode located at a first location in a microfluidic channel of the test strip; monitoring the applied periodic signal with a second electrode located at a second location in the microfluidic channel; and using a third electrode located at a third location in the microfluidic channel as a reference electrode, wherein each of the first electrode, the second electrode and the third electrode has a reconfigurable function. The method further involves: collecting the bodily fluid sample in the microfluidic channel; continuing to apply the periodic signal, monitor the periodic signal and use the third electrode as a reference electrode, while collecting the bodily fluid sample; switching configurations of the first electrode, the second electrode and the third electrode, while collecting the bodily fluid sample; and determining that the bodily fluid sample is sufficient for analyzing, based at least in part on the applied and monitored periodic signal. In some embodiments, the method may further involve determining at least one of a sample flow rate and a sample viscosity, by comparing signals generated with various electrode configurations.

In another aspect of the present disclosure, a method of assessing consistency and reducing the sensitivity of a measurement of a bodily fluid sample on a test strip with at least four electrodes involves: applying a periodic signal with at least some of the at least four electrodes, wherein the at least four electrodes are located at different locations in a microfluidic sample chamber of the test strip; monitoring the periodic signal with at least some of the at least four electrodes; collecting the bodily fluid sample on the test strip; identifying a period of stability in the monitored signals; and initiating measurement of the bodily fluid sample, based on the identified period of stability.

Optionally, the method may also include determining a sample flow rate and a viscosity by comparing signals generated with various sets of electrodes. The method may also include recommending a method for collecting the bodily fluid sample to a user, based at least in part on the monitored signals.

These and other aspects and embodiments are described in greater detail below, in relation to the attached drawing figures.

BRIEF DESCRIPTION OF THE DRAWINGS

FIGS. 1A-1C illustrate one end of a saliva test strip, showing an empty microfluidic channel (FIG. 1A), a partially filled channel (FIG. 1B), and a filled channel (FIG. 1C);

FIG. 2A illustrates one end of a saliva test strip with a microfluidic channel partially filled with sample fluid, according to one embodiment;

FIG. 2B is a line graph illustrating a reading of a monitored electrode signal from the saliva test strip of FIG. 2A;

FIG. 3A illustrates one end of a saliva test strip with a microfluidic channel and four electrodes, according to one embodiment;

FIG. 3B includes multiple line graphs representing multiple readings of multiple monitored electrode signals from the saliva test strip of FIG. 3A;

FIG. 4A illustrates a saliva test strip with multiple concentric electrodes located within the microfluidics of the strip, according to one embodiment;

FIG. 4B includes multiple line graphs representing multiple readings of multiple monitored electrode signals from the saliva test strip of FIG. 4A.

DETAILED DESCRIPTION

Figure 5:
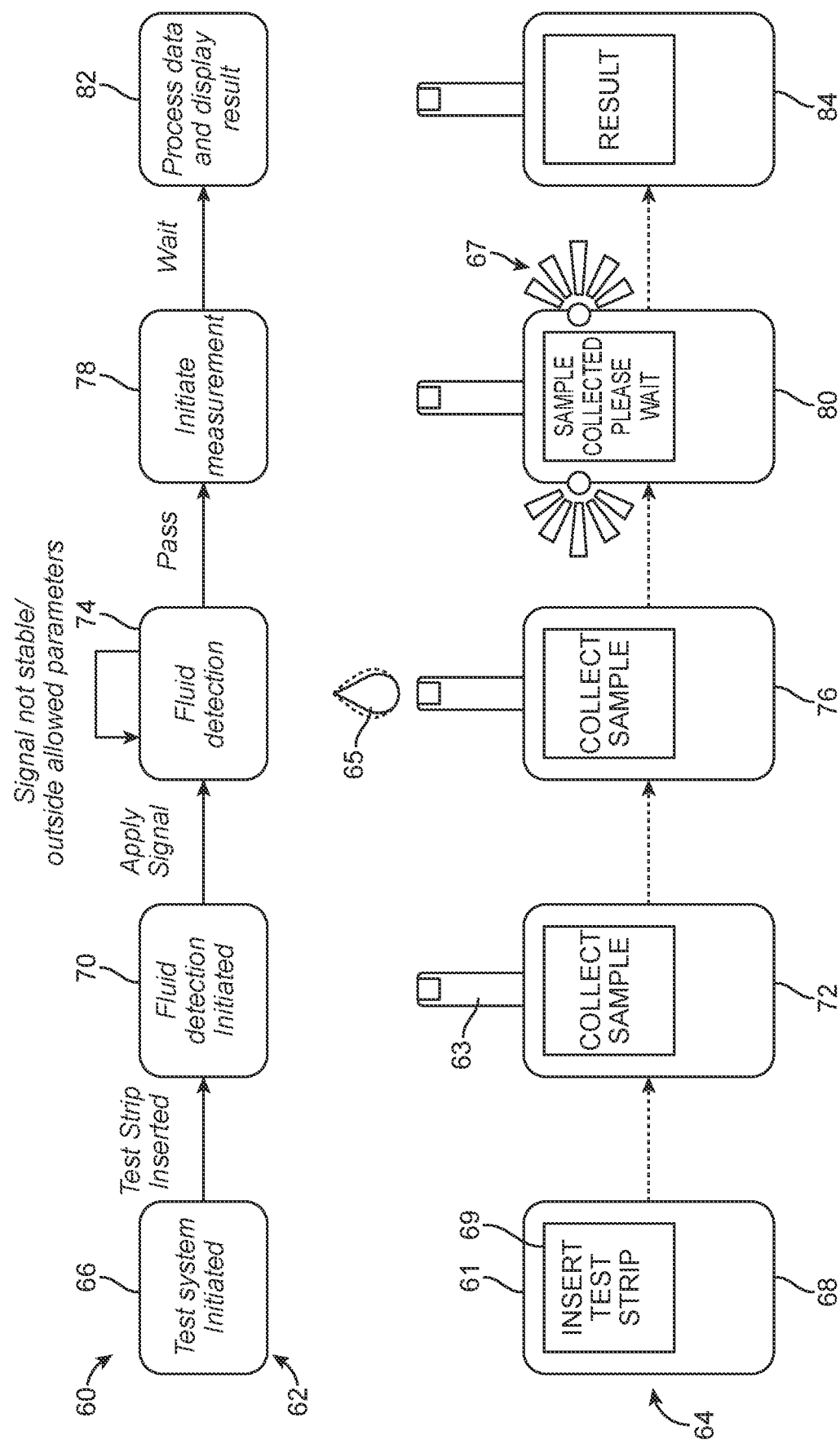
FIG. 5 is flow diagram illustrating a method for collecting and analyzing a bodily fluid sample and providing prompts and information to a user, according to one embodiment.

The assignee of the present application has filed previous patent applications describing systems, methods and devices for testing, measuring and analyzing saliva, to measure a subject's hydration level, as well as for measuring other substances (e.g., sweat) and/or physiological parameters in a human or animal subject. These previous patent applications include U.S. patent application Ser. No. 16/197,530 (U.S. Pub No. 2019/0150836), titled "Saliva Testing System," and filed Nov. 21, 2018; 62/744,389, titled "Ion Selective Sensor," and filed Oct. 11, 2018; and 62/872,339, titled "Saliva Test Strip and Method," and filed on Jul. 10, 2019. All of these patent applications are hereby incorporated by reference into the present application, and they may be referred to herein as "the Incorporated Applications."

The present application adds to the technologies in the Incorporated Applications by describing a method, device and system for determining whether a bodily fluid sample has completely and stably filled sampling fluidics on a test strip. This determination is made before initiating measurement of the fluid sample, to ensure that a measurement is not conducted on an inadequate sample.

One solution to the challenges described above in the background section is a bodily fluid analysis test strip—part of a bodily analysis system—that is configured to address these issues (e.g., fluidics size, shape and/or materials), and enhance the operation of the bodily analysis system for a given fluid, such as saliva. The assignee of the present application described such a test strip in co-pending U.S. Provisional Patent Application No. 62/872,339, referenced above.

Another possible solution for some of the challenges of point-of-care testing of saliva and other bodily fluids would be for some part of the bodily fluid analysis system to determine that a collected sample is sufficient for testing. Typically, measurement initiation is triggered on disposable test strips when sample fluid bridges a gap between two electrodes, thus completing a circuit and indicating that enough sample has entered the test strip. The electrodes are typically located at the opposite end of the test strip from the sampling fluidics (i.e., the end of the strip on which the sample is collected). This solution is appropriate for more consistent fluids, like blood, where flow through the test strip fluidics is relatively uniform and predictable.

Due to the variable (and potentially high) viscosity of saliva, however, bridging between two electrodes on a test strip can occur without complete channel filling (see FIG. 1B) or can be transient in nature. As such, additional time may be required to allow a sample fluid to adequately fill a test strip to allow for measurement of the sample. It can be very challenging for a user of such a test strip/test system to determine whether enough saliva has been collected on a given test strip to allow for an accurate measurement.

The present application describes various embodiments and features of a method, device and system for analyzing a sample of saliva or other bodily fluid (e.g., sweat, blood, etc.). Specifically, the embodiments described herein provide a method of assessing a saliva sample to determine if it is sufficient (and has sufficiently filled microfluidics of a test strip) to allow for an accurate measurement of the sample. Although the following disclosure focuses on the analysis of saliva, the embodiments described below, or variations of those embodiments, may be used for analysis of any other bodily fluid, such as sweat, blood, urine or the like.

Referring to FIGS. 1A-1C, the tip of a saliva analysis test strip 10 is shown in three different states of fluid sample collection. FIG. 1A shows the test strip 10 with its microfluidic channel 12 empty—in other words, no fluid sample has been collected. Also shown are the three electrodes 14 of the test strip 10.

FIG. 1B shows the test strip 10 with the microfluidic channel 12 partially filled with a saliva sample 16 (or other bodily fluid sample in alternative embodiments). As mentioned above, the image in FIG. 1B demonstrates one of the challenges with using a typical test strip 10 in a point-of-care saliva analysis—i.e., the sample 16 may bridge across the electrodes 14, even though it is not enough sample 16 to fill the channel 12. FIG. 1C shows the channel 12 completely filled with the saliva sample 16. Again, with a typical test strip 10, it may be difficult or impossible to tell the difference between the partial filling of FIG. 1B and the complete filling of FIG. 1C.

Referring now to FIGS. 2A and 2B, one embodiment of a method for assessing a saliva sample 26 on a test strip 20 is illustrated. In this embodiment, the test strip 10 includes a substrate, a microfluidic channel 22 (or "sampling microfluidics"), and three electrodes 24a, 24b, 24c (although alternative embodiments may include more than three). The electrodes 24a, 24b, 24c have fixed functions and are positioned at different locations along the length of the test strip's microfluidic channel 22. Prior to and during sample measurement, a first electrode 24a applies a periodic signal, a second electrode 24b monitors the signal, and a third electrode 24c acts a reference electrode. The monitored signal is evaluated by a handheld sample analysis device (not pictured) that is coupled with the test strip 20. As the saliva sample 26 is collected in the microfluidic channel 22, it will bridge all three electrodes 24a, 24b, 24c but may continue to shift within the microfluidic channel 22. FIG. 2B shows a line graph that illustrates this sample shifting as an unstable period 30. After the sample 26 stops shifting, the line on the graph 28 stabilizes in a stable period 32. The handheld analysis device monitors the electrode signals to wait for the stable period 32. In this embodiment, measurement of the sample 26 by the analysis device will only begin after a period of consistency in the monitored signal—i.e., the stable period 32—within a pre-determined range of acceptable variation.

Referring now to FIGS. 3A and 3B, in an alternative embodiment, the electrodes 44a-44d of a test strip 40 with a microfluidic channel 42 do not have a fixed function, but instead have their function rapidly reconfigured during sample collection. In this embodiment, the test strip 40 includes four electrodes 44a-44d, but alternative embodiments may have any other suitable number. At any given time, one of the electrodes 44a-44d applies a periodic signal, another of the electrodes 44a-44d monitors this signal, and yet another electrode 44a-44d acts a reference. Which electrode 44a-44d has each function, however, may change as frequently as many times per second. Referring to FIG. 3B, a period of consistency in the monitored signal within and between electrode configurations, as shown in the line graphs 45, 46, 47, is necessary prior to measurement initiation. In addition to the benefits of the method described above, this embodiment of the method allows sample flow rate and viscosity to be determined, by assessing time-of-flight of the sample. These parameters may optionally be used in a saliva measurement algorithm, for example to adjust sample analysis results for flow rate and/or viscosity.

In another embodiment, illustrated in FIGS. 4A and 4B, a biological fluid analysis test strip 50 includes a microfluidic channel 52 and multiple sets of concentric electrodes 54a-54d in the microfluidic channel 52. Each set of electrodes 54a-54d is configured to independently assess signal fluctuation during sample collection. As illustrated in the line graphs 55, 56, 57 of FIG. 4B, a period of consistency in the monitored signal of each set of electrodes 54a-54d, within a pre-determined range of acceptable variation, is required prior to initiation of the sample measurement. The difference between the signal measured by each set of electrodes 54a-54d during sample collection may be used to assess sample flow rate and viscosity. Additionally, this electrode structure may reduce the sensitivity of sample measurement to the volume of sample within the microfluidic channel 52 or localized variation within the microfluidic channel 52.

For all method embodiments described herein, the ongoing signal monitoring, prior to and during sample collection, may be used to communicate the current state of the sample being collected (e.g., sufficient fluid, insufficient fluid, faulty sample) to a user, through noise, vibration and/or a visual signal on the testing system or a connected device.

FIG. 5 illustrates a method 60 for collecting a saliva (or other bodily fluid) sample using a test strip inserted into a saliva analysis device. FIG. 5 depicts a series of method steps 62 and a corresponding series of instructions 64 provided to a user on a display screen 69 of a handheld biological fluid analysis device 61. Following the method steps 62 first, according to this embodiment, the user first initiates the test system 66 (e.g., the handheld device 61). Once a test strip 63 is inserted into the handheld device 61 and a sample is collected on the test strip 63, the system initiates fluid detection 70. If the fluid signal is not stable, fluid detection continues 74 until a stable signal is detected. If it is not detected, the user is told that the sample is insufficient. Once a stable fluid signal is acquired, sample measurement is initiated 78. Finally, measurement data is processed, and the system displays one or more results of the fluid sample measurement 82 (saliva or other fluid).

Turning now to how this method appears to the user of the handheld device 61, the series of instructions 64 will be explained. After being initiated, the first step 68 on the handheld device 61 is to display an instruction on the display screen 69, instructing the user to insert a test strip 63 into the device 61. In the next step 72, the user has inserted the test strip 63 and is instructed on the screen 69 to collect a sample. The user then collects the saliva (or other bodily fluid) sample 65 in the sample collection step 76, for example, by collecting saliva directly on the free end of the test strip 63 by applying it to the user's tongue. If insufficient sample fluid has been collected, a visual signal is displayed on the screen of the analysis device (not illustrated), indicating that insufficient sample has been collected. As the sample is collected, the "Collect Sample" signal remains displayed on the screen, as an ongoing prompt to the user to continue to collect more saliva with the test strip 63. Once enough fluid has been collected and consistency has been confirmed by one of the above-described methods, a tone 67 is emitted by the device, and the message displayed on the screen changes to reflect that enough sample has been collected 80. These notifications tell the user that she can stop collecting saliva on the test strip 63. The analysis device then conducts its measurements, as indicated on the screen. When analysis is completed, the results are shown on the device 84.

Although the above description is believed to be complete and accurate, various changes to any of the embodiments and features described herein may be made, without departing from the scope of the invention. For example, the order of method steps may be altered, one or more method steps may be eliminated, and/or one or more methods steps may be added, in any given embodiment.

We claim:

1. A method of assessing a bodily fluid sample on a test strip, the method comprising:
    applying a periodic signal with a first electrode located at a first location in a microfluidic channel of the test strip;
    monitoring the applied periodic signal with a second electrode located at a second location in the microfluidic channel;
    using a third electrode located at a third location in the microfluidic channel as a reference electrode, wherein each of the first electrode, the second electrode and the third electrode has a fixed function;
    collecting the bodily fluid sample in the microfluidic channel while continuing to apply the periodic signal, monitor the periodic signal and use the third electrode as a reference electrode; and
    determining that the bodily fluid sample is a sufficient volume for analyzing by identifying a period of stability in the monitored periodic signal, based at least in part on the applying and monitoring of the periodic signal.

2. The method of claim 1, wherein the periodic signal fluctuates depending on a volume of the bodily fluid sample and a movement of the bodily fluid sample through the microfluidic channel, and wherein a period of stability in the monitored periodic signal is required before determining that the bodily fluid sample is sufficient.

3. The method of claim 1, further comprising initiating an analysis of the bodily fluid sample, based on the determining step.

4. The method of claim 1, further comprising, before the determining step:
    determining that the bodily fluid sample is insufficient for analyzing; and
    indicating to a user to collect more of the bodily fluid sample on the test strip.

5. The method of claim 4, wherein determining that the bodily fluid sample is insufficient comprises identifying in the monitored periodic signal one of a period of instability or a period of stability outside of a predetermined range.

6. The method of claim 4, wherein indicating to the user comprises providing at least one of an auditory signal, a vibration or a visual signal in a bodily fluid analysis device directly connected with the test strip or a separate device wirelessly connected with the bodily fluid analysis device.

7. The method of claim 1, further comprising indicating to a user that the bodily fluid sample is sufficient by providing at least one of an auditory signal, a vibration or a visual signal in a bodily fluid analysis device directly connected with the test strip or a separate device wireless connected with the bodily fluid analysis device.

8. The method of claim 1, wherein the bodily fluid sample comprises a bodily fluid selected from the group consisting of saliva, sweat, blood and urine.

9. A method of assessing a bodily fluid sample on a test strip, the method comprising:
    applying a periodic signal with a first electrode located at a first location in a microfluidic channel of the test strip;
    monitoring the applied periodic signal with a second electrode located at a second location in the microfluidic channel;
    using a third electrode located at a third location in the microfluidic channel as a reference electrode, wherein each of the first electrode, the second electrode and the third electrode has a reconfigurable function;
    collecting the bodily fluid sample in the microfluidic channel while continuing to apply the periodic signal, monitor the periodic signal and use the third electrode as a reference electrode;
    reconfiguring the functions of the first electrode, the second electrode and the third electrode, while collecting the bodily fluid sample;
    continuing to apply the periodic signal, monitor the periodic signal and use a reference electrode with the reconfigured functions of the first, second, and third electrodes; and
    determining that the bodily fluid sample is sufficient for analyzing, based at least in part on the applied and monitored periodic signal.

10. The method of claim 9, further comprising determining at least one of a sample flow rate and a sample viscosity, by comparing signals generated with various electrode configurations.

11. The method of claim 9, further comprising, before the determining step:
    determining that the bodily fluid sample is insufficient for analyzing; and
    indicating to a user to collect more of the bodily fluid sample on the test strip.

12. A method of assessing a measurement of a bodily fluid sample on a test strip with at least four electrodes, the method comprising:

applying a periodic signal with at least some of the at least four electrodes, wherein the at least four electrodes are located at different locations in a microfluidic sample chamber of the test strip;

monitoring the periodic signal with at least some of the at least four electrodes to collect at least two monitored signals;

collecting the bodily fluid sample on the test strip;

identifying a period of stability in the monitored signals; and initiating measurement of the bodily fluid sample, based on the identified period of stability.

13. The method of claim 12, further comprising determining a sample flow rate and a viscosity by comparing signals generated with various sets of electrodes.

14. The method of claim 12, further comprising recommending a method for collecting the bodily fluid sample to a user, based at least in part on the monitored signals.

* * * * *

UNITED STATES PATENT AND TRADEMARK OFFICE
CERTIFICATE OF CORRECTION

PATENT NO. : 11,703,436 B2
APPLICATION NO. : 17/159770
DATED : July 18, 2023
INVENTOR(S) : Efstratios Skafidas et al.

It is certified that error appears in the above-identified patent and that said Letters Patent is hereby corrected as shown below:

On the Title Page

On Page 2, Column 2, (Item (56) U.S. Patent Documents), Line 12: Delete "Abeyrathne" and insert -- Abeyrathne et al. --.

On Page 2, Column 2, (Item (56) Other Publications), Line 27: Delete "an" and insert -- on --.

In the Claims

On Column 8, Line 14: In Claim 5, delete "instability" and insert -- instability, --.

Signed and Sealed this
Nineteenth Day of September, 2023

Katherine Kelly Vidal
*Director of the United States Patent and Trademark Office*